United States Patent [19]

Cody et al.

[11] Patent Number: 5,660,859

[45] Date of Patent: Aug. 26, 1997

US005660859A

[54] GELLING AGENT FOR POLYETHYLENE GLYCOL

[75] Inventors: Sharon L. Cody, Philadelphia; Michael R. Hoy, Sellersville; Eric J. Walter, Philadelphia, all of Pa.

[73] Assignee: McNeil-PPC, Inc., Skillman, N.J.

[21] Appl. No.: 366,271

[22] Filed: Dec. 29, 1994

[51] Int. Cl.$^6$ .................. A61K 9/48; A61K 9/64
[52] U.S. Cl. .................. 424/451; 424/401; 424/456
[58] Field of Search .................. 424/401, 451, 424/456, 441

[56] References Cited

U.S. PATENT DOCUMENTS

| | | | |
|---|---|---|---|
| 1,970,396 | 8/1934 | Scherer | 18/21 |
| 2,288,327 | 6/1942 | Scherer | 18/21 |
| 2,318,718 | 5/1943 | Scherer | 18/21 |
| 3,851,051 | 11/1974 | Miskel et al. | 424/37 |
| 4,028,024 | 6/1977 | Moreland | 425/133.1 |
| 4,428,927 | 1/1984 | Ebert et al. | 424/37 |
| 4,467,921 | 8/1984 | Greenland et al. | 206/524.4 |
| 4,486,412 | 12/1984 | Shah et al. | 424/156 |
| 4,609,403 | 9/1986 | Wittwer et al. | 106/122 |
| 4,690,822 | 9/1987 | Uemura et al. | 424/455 |
| 4,708,834 | 11/1987 | Cohen et al. | 264/4.3 |
| 4,795,642 | 1/1989 | Cohen et al. | 424/455 |
| 4,844,906 | 7/1989 | Hermelin et al. | 424/456 |
| 4,883,660 | 11/1989 | Blackman et al. | 424/78 |
| 4,935,243 | 6/1990 | Borkan et al. | 424/441 |
| 5,071,643 | 12/1991 | Yu et al. | 514/570 |
| 5,085,033 | 2/1992 | Graham | 53/436 |
| 5,146,730 | 9/1992 | Sadek et al. | 53/454 |

FOREIGN PATENT DOCUMENTS

| | | |
|---|---|---|
| 0 243 930 A1 | 11/1987 | European Pat. Off. . |
| 0 266 796 A1 | 5/1988 | European Pat. Off. . |
| 25 05 755 | 8/1975 | Germany . |
| 298351 A5 | 2/1992 | Germany . |
| 420178 A1 | 7/1993 | Germany . |
| WO 91/07950 | 6/1991 | WIPO . |
| 95/04527 | 2/1995 | WIPO . |

OTHER PUBLICATIONS

The U.S. Pharmacopeia, The National Formulary, USP 23, NF 18, pp. 1830–1835, (1995).

EPO Search Report for EP Appln. No. 95 30 9508.

Chemical Abstracts, vol. 122, No. 18, Abst. No. 164840 (1989).

Gafitanu et al., "Investigations on the Cutaneous Bioavailability of Alpha–Chemotryspin from Ointments", *Rev. Med. Chir. Soc. Med.Nat. IASI*, vol. 93, No. 2, pp. 211 and 353–6 (1989).

H. Seager, Pharmaceutical Technology, Sep. 1985, Soft Gelatin Capsules: A Solution to Many Tableting Problems, pp. 84, 86, 88, 90, 92, 94, 96, 98, 100, 102, & 104 Remington's Pharmaceutical Sciences, 18th Ed. Chap. 83, pp. 1539–1540 (1990).

*Primary Examiner*—Thurman K. Page
*Assistant Examiner*—Sharon Howard
*Attorney, Agent, or Firm*—Bernard F. Plantz

[57] ABSTRACT

The present invention relates to gelling liquid polyethylene glycol at room temperature with calcium acetate.

16 Claims, No Drawings

GELLING AGENT FOR POLYETHYLENE GLYCOL

FIELD OF THE INVENTION

The present invention relates to gelling liquid polyethylene glycol at room temperature to produce a substantially translucent gel suitable for use in pharmaceutical or cosmetic products.

BACKGROUND OF THE INVENTION

In recent years soft gelatin or soft elastic gelatin capsules have become a popular dosage form for the oral delivery of therapeutic agents, especially over-the-counter pharmaceuticals. These capsules are typically filled with a liquid containing the active ingredient. Because of their soft, elastic character, some patients view these capsules as easier to swallow than conventional tablets or hard gelatin capsules. Since the dosage form is generally swallowed, it is not necessary to flavor or otherwise mask the often unpleasant taste of the pharmaceutical. Soft gelatin capsules are also preferred to bulk liquids because they are easier to transport and they avoid the need for the patient to measure a prescribed amount of the liquid before dosing.

The fill material used in a soft gelatin capsules generally contains a pharmaceutical dissolved or dispersed in a carrier that is compatible with the capsule wall. In addition to liquids, U.S. Pat. No. 4,935,243 to L. Borkan et al. suggests that the fill material may take the form of a semi-solid, solid, or gel. Conventional tablets or pellets containing an active ingredient are examples of solid fill materials that may be encapsulated within a soft gelatin capsule.

Semi-solid (dispersion) fill material are discussed in U.S. Pat. No. 4,486,412 to D. Shah et al. A fill material containing an orally-administered antacid salt that is dispersed in a water-free, liquid carrier containing a major proportion of one or more polyalkylene glycols and a minor proportion of a $C_2$–$C_5$ polyol, such as propylene glycol or glycerin. The carrier forms a stable dispersion of the antacid salt and coats the antacid particles, thereby rendering them non-reactive with the soft gelatin capsule wall.

U.S. Pat. No. 4,708,834 to Cohen et al. suggests a controlled release pharmaceutical dosage form comprising a soft gelatin capsule that encloses a water-soluble or dispersible gelled polymer matrix. The fill material comprises an aqueous solution or dispersion of a polysaccharide gum, the pharmaceutical active and, optionally, an alcohol. The liquid fill is introduced into a soft gelatin capsule that contains a cationic gelling agent, which gels the liquid fill after it has been incorporated into the capsule shell. The alcohol used in the fill includes liquid polyethylene glycols, lower alkanols, $C_2$–$C_4$ polyols and mixtures thereof.

U.S. Pat. No. 5,071,643 to M. Yu et al. also discusses the use of polyethylene glycols (PEG) as a fill material in soft gelatin dosage forms. PEGs having an average molecular weight between 400–600 are preferred for liquid fills, between 800–10,000 for semi-solid fills and between 10,000–100,000 for solid fills.

PCT Publication No. WO 91/07950 describes a soft or two-piece hard gelatin capsule shell containing benzodiazepine dissolved or suspended in a gel. The gel contains by weight at least 63% of polyethylene glycol 600, at least 4% of polyethylene glycol 4000 or 6000, and at least 21% of polyethylene glycol 600–4000. This gel fill cannot be expelled with a syringe at ambient temperature and therefore avoids the reported abuse of liquid filled capsules by intravenous drug abusers.

*Remington's Pharmaceutical Sciences*, 18th ed, Chapter 83, pp. 1539–40 (1990), reports that gelling agents used to make gels for pharmaceutical and cosmetic products, include sodium alginate and triethanolamine.

A need exists for a technique for gelling liquid polyethylene glycols at room temperature to produce a substantially translucent gel, suitable for use in the production of cosmetics or pharmaceutical dosage forms.

SUMMARY OF THE INVENTION

The present invention provides a technique for gelling liquid polyethylene glycols at room temperature. The gel is suitable for use as a fill material in a soft gelatin capsule pharmaceutical dosage form, a carrier for a pharmaceutical in a topical formulation, or as a base for a cosmetic or dental care product.

The gel comprises a liquid polyethylene glycol, water and an effective amount of calcium acetate to gel the glycol. A effective amount of an active ingredient, such as a deodorant or a pharmaceutical, is dissolved or suspended in the gel.

The gel of the present invention has a substantially translucent appearance, and when used to fill a soft gelatin capsule or as base in a cosmetic care product, the resulting product has an elegant, substantially translucent appearance.

DETAILED DESCRIPTION OF THE PREFERRED EMBODIMENTS

The present invention provides a technique for gelling liquid polyethylene glycols at room temperature. The resulting gel is substantially translucent and may be used as a carrier for a pharmaceutical in a soft gelatin capsule, topical formulation or two-piece hard gelatin capsule.

Since calcium acetate spontaneously gels liquid polyethylene glycol at room temperature, the present invention provides a number of processing advantages. No heating or cooling is required, so the manufacture process is simple and inexpensive. The resulting gel also has relatively few components, which helps to reduce the number of mixing steps in the process.

The liquid polyethylene glycol has an average molecular weight of about 600 or less, preferably about 200 to about 600, and most preferably about 300 to about 400. A minor proportion of water is also used in conjunction with the polyethylene glycol. The gel generally comprises by weight about 40 to about 80, preferably about 50 to about 70, percent polyethylene glycol and about 1 to about 40, preferably about 5 to about 25, percent water. Unless otherwise stated, the percentages recited herein are by weight of the total weight of the gel fill material, i.e., both the gel and active ingredient.

The calcium acetate is employed in an amount effective to form a gel at room temperature that has the desired viscosity or gel strength. Generally the gel contains by weight from about 0.5 to about 10, preferably about 0.5 to about 5 percent calcium acetate. The calcium acetate may me used in either an anhydrous or hydrated form.

The viscosity or gel strength is dependent upon the end use of the gel. For pharmaceutical applications, such as for use as the fill material in a soft gelatin capsule, the gel should be sufficiently viscous so that it cannot be expelled at room temperature with a syringe. This feature helps to protect against possible intravenous abuse of the drug as well as product tampering. For topical pharmaceutical and/or cosmetic applications, such as for use as a spreadable gel, ointment or lotion, the gel need not be as viscous.

The viscosity or gel strength is also affected by an increase or decrease in the amount of shear applied in the manufacturing process. It was found that the amount of shear and the length of mixing have an effect on the strength of the gel. A large amount of shear decreases the strength of the gel and, likewise, a minimal amount of shear increases the strength of the gel. Also, it was found that the best way to maximize the strength of the gel is by decreasing shear and, most preferably, by eliminating any mixing. Therefore, a dual head filling process directly into the soft gelatin capsule without any mixing is the best means for achieving a strong gel fill material suitable for soft gelatin capsule applications. A manufacturing process with sufficient mixing is the best means for achieving a low viscosity gel material suitable for topical applications.

Solubilizing agents may also be employed to enhance the solubility or dispersibility of the active ingredient in the gel. Suitable agents include:

| % (wt.) | Component |
| --- | --- |
| 0–15 | Propylene Glycol |
| 0–15 | Glycerin |
| 0–10 | Ethanol |
| 0–20 | Sodium Acetate (anhydrous, hydrate) |

The pharmaceutical active used in the present invention can be any medication which can be administered orally to transmit the active agent into the gastrointestinal tract and into the bloodstream at therapeutically effective levels.

The pharmaceutical active(s) is present in the dosage form in a therapeutically effective amount, which is an amount that produces the desired therapeutic response upon oral administration, and can be readily determined by one skilled in the art. In determining such amounts, the particular compound being administered, the bio-availability characteristics of the compound, the dose regiment, the age and weight of the patient, and other factors must be considered. Pharmaceuticals suitable for use in the invention include acetaminophen, famotidine, chlorpheniramine, pseudoephedrine, dextromethorphan, diphenhydramine, brompheniramine, phenylpropanolamine, clemastine, terfenadine, astemizole, loratadine, pharmaceutically acceptable salts thereof and mixtures thereof.

Various other pharmaceutically acceptable excipients may be included in the pharmaceutical dosage form, such as preservatives, e.g., methyl- or propylparaben, and coloring agents.

In a preferred embodiment, a fill for a soft gelatin capsule containing about 250 mg/ml of acetaminophen, comprises by weight from about 23 to about 27 percent acetaminophen, from about 60 to about 70 percent PEG 400, from about 10 to about 20 percent water, and from about 1 to about 3 percent calcium acetate.

Suitable active ingredients for use in topical pharmaceutical formulations include antifungals, anti-inflammatory corticosteroids, antibiotics, otic-active ingredients, ophthalmic-active ingredients, anti-acne medicaments, and nasal-active ingredients.

Suitable active ingredients for use in cosmetic and dental care products include deodorants, sodium fluoride, antiperspirants, perfumes, and skin moisturizers.

The amount of the active ingredient, whether a pharmaceutical or an active in a cosmetic, employed in the gel will vary depending on the potency of the active and the desired strength of the dosage form or product. Generally, the active ingredient comprises about 0.1 to about 40, preferably about 0.2 to about 30, percent by weight of the total gel composition.

In a preferred embodiment of the present invention, the active ingredient, at the desired dosage, must also be sufficiently soluble or dispersible in the gel so that the resulting composition has a turbidity of less than about 1300 NTU (Nephelometric Turbidity Unit).

The gel is prepared by first forming an aqueous calcium acetate solution. The active ingredient(s) is then mixed with the liquid polyethylene glycol and the solubizing agent, if any, being used in the formulation. The aqueous calcium acetate solution is combined with the actives mixture at room temperature. It can be mixed gently for lower viscosity gels (spreadable). For higher viscosity gels (semi-solid like), the calcium acetate solution and the actives mixture are combined in a dual head filling mechanism without any additional mixing. The mixture resulting from the dual head filling device is then left undisturbed for about 5 to about 60 minutes to effect gelling.

The fill material of the present invention may be used in commercially available soft gelatin capsules, such as those commercially available from R. P. Scherer or Banner Pharmacaps. Various sizes, shapes, and colors can be used to accommodate different levels of active ingredients. The walls of the capsules have a substantially translucent or clear appearance. When the fill material of the present invention is introduced into the capsule and gelled, the resulting dosage form has an elegant, translucent or clear appearance.

If a soft gelatin capsule dosage form is being prepared, the gel is formed at ambient room temperature in the capsule after the two component mixture, namely the PEG/actives mixture and the calcium acetate solution, are injected separately. The needle on the syringe is used to puncture one end of the soft gelatin capsule so that the appropriate amount of the two component mixtures may be injected by hand. The capsule with fill material is allowed to set undisturbed at ambient room temperature to effect gelling.

The fill material may also be introduced into the soft gelatin capsule using encapsulation equipment known in the art, such as that described in U.S. Pat. No. 4,028,024 to Moreland, which is hereby incorporated by reference. Such equipment, however, requires the use of a dual head to introduce the two component mixtures into the gelatin shell as separate streams.

Further details of the use of gel as a fill material in a soft gelatin capsule may be found in copending, commonly assigned patent application Ser. No. 08/366,945, filed on even date herewith, entitled "Soft Gelatin Pharmaceutical Dosage Form," which is hereby incorporated by reference.

Specific embodiments of the present invention are illustrated by way of the following examples. This invention is not confined to the specific limitations set forth in these examples, but rather to the scope of the appended claims. Unless otherwise stated, the percentages, parts and ratios given below are by weight.

The turbidity of the fill materials described in the following examples was measured using a Hach Ratio/XR Turbidimeter. The United States Pharmacopedia defines turbidance as the light-scattering effect of suspended particles and turbidity as the measure of the decrease in the incident beam intensity per unit length of a given suspension. This instrument measures turbidity within a range of 0.00 to 2000 NTU. As a point of reference, the turbidity of water is zero. Samples of the fill materials, approximately 8 mL, were transferred to Fisher Brand 13×100 mm culture tubes immediately after manufacture. The fill material samples were stored at ambient room temperature since they were made several days in advance. The outer surface of each of the sample culture tubes was treated with silicone oil just prior to measuring the turbidity. The turbidity of the samples was measured at ambient room temperature. The turbidity of two sample tubes of each fill material was measured and the average of the results is reported.

EXAMPLE 1

This Example reports the results of an experiment wherein different salts were evaluated as potential gelling agents for liquid polyethylene glycol at room temperature.

For each of the tested salts, the composition shown below was prepared at room temperature by solubilizing the salt in water and then mixing with PEG 400 to see if a gel would form at ambient room temperature.

| Component | Amount (% w/w) |
| --- | --- |
| PEG 400 | 61.54 |
| Salt | 7.69 |
| Water | 30.77 |

The following summarizes the results of the experiment:

| Salt | Cation | Result |
| --- | --- | --- |
| Calcium Acetate | $Ca^{2+}$ | G |
| Sodium Acetate | $Na^{1+}$ | NG |
| Potassium Acetate | $K^{1+}$ | NG |
| Zinc Acetate | $Zn^{2+}$ | NG |
| Ammonium Acetate | $NH_4^{1+}$ | NG |
| Magnesium Acetate | $Mg^{2+}$ | NG |
| Barium Acetate | $Ba^{2+}$ | NG |
| Calcium Propionate | $Ca^{2+}$ | NG |

G = gel formed
NG = no gel formation
Note: Zinc acetate is relatively insoluble in water and the resulting solution was supersaturated.

The above unexpectedly demonstrates that calcium acetate gels liquid polyethylene glycol whereas the other tested salts do not have this effect.

EXAMPLE 2

This Example discloses a composition of the present invention which was gelled at room temperature with calcium acetate. The gel contained:

| Component | Amount (% w/w) |
| --- | --- |
| Calcium Acetate | 5.0 |
| Water | 17.0 |
| PEG 400 | 75.0 |
| Glycerin | 3.0 |

The sample was prepared as follows:

1) Add calcium acetate to water and mix until the calcium acetate is dissolved.
2) Add PEG 400 and mix.
3) Add glycerin and mix.
4) Gel forms at room temperature after about 2 minutes. The resulting gel had a translucent appearance.

EXAMPLE 3

This Example discloses a acetaminophen-containing composition of the present invention which was gelled at room temperature with calcium acetate. The gel contained:

| Component | Amount (% w/w) |
| --- | --- |
| Calcium Acetate | 1.5 |
| Water | 6.0 |
| PEG 400 | 61.2 |
| Ethanol | 6.8 |
| Acetaminophen | 24.5 |

The sample was prepared as follows:

1) An aqueous solution containing 20% (wt.) of calcium acetate was prepared.
2) The following ingredients were mixed to form an actives mixtures:

| Component | Amount (% w/w) |
| --- | --- |
| Acetaminophen | 26.5 |
| PEG 400 | 66.2 |
| Ethanol | 7.3 |

3) One part of the solution of step 1) was mixed with nine parts of the mixture of step 2). The resulting mixture was allowed to gel at room temperature.
The resulting gel had a translucent appearance.

EXAMPLE 4

This Example discloses a composition of the present invention which was gelled at room temperature with calcium acetate. The gel contained:

| Component | Amount (% w/w) |
| --- | --- |
| PEG 400 | 80.36 |
| Calcium Acetate | 1.78 |
| Water | 17.86 |

The gel was prepared as follows:

1) Weigh calcium acetate and water. Sonicate/mix to dissolve calcium acetate.
2) In a separate beaker, weigh PEG 400 and stir.
3) Add calcium acetate solution to PEG 400 while mixing. Continue to mix until system gels.
4) Sonicate gel to remove air.

The fill material was substantially clear and had a turbidity of 195 NTU, although some air was noted in the tested samples.

EXAMPLE 5

This Example discloses a fill material of the present invention containing 200 mg/mL of acetaminophen which was gelled at room temperature with calcium acetate. The fill material contained:

| Component | Amount (% w/w) |
| --- | --- |
| Acetaminophen | 18.24 |
| PEG 400 | 65.70 |

-continued

| Component | Amount (% w/w) |
|---|---|
| Calcium Acetate | 1.46 |
| Purified Water | 14.60 |

The samples was prepared as follows:

1) Weigh calcium acetate and water. Sonicate/mix to dissolve calcium acetate.

2) In a separate beaker, weigh active and PEG 400. Mix to form active/PEG slurry.

3) Add calcium acetate solution to PEG while mixing. Continue to mix until system gels.

4) Sonicate gel to remove air.

The fill material was substantially translucent and had a turbidity of 865 NTU, although some air was noted in the tested samples.

The resulting fill material could be expelled at room temperature with a syringe having an 18 gauge needle because the strength of the gel was weakened by the mixing step. It was found that the gel strength can be maximized by eliminating the mixing step. The sample was prepared a second time by first hand-filling a soft gelatin capsule shell with the active/PEG slurry with a syringe. Then the calcium acetate solution was injected into the capsule shell containing the active/PEG slurry. The resulting mixture was allowed to gel at room temperature in the capsule shell. The capsule was then cut open with a scalpel and the fill material was observed to be a solid material.

Various modifications can be made to the above-described embodiments without departing from the spirit and scope of the present invention.

What is claimed is:

1. A gel composition, comprising:
   about 40 to about 80 percent polyethylene glycol having an average molecular weight of about 600 or less;
   about 1 to about 40 percent water; and
   about 0.5 to about 10 percent calcium acetate, by weight of the gel.

2. The composition of claim 1 wherein said polyethylene glycol has an average molecular weight of about 200 to about 600.

3. The composition of claim 1 comprising:
   about 50 to about 70 percent polyethylene glycol;
   about 5 to about 25 percent water; and
   about 0.5 to about 5 percent calcium acetate, by weight of the gel.

4. The composition of claim 3 wherein polyethylene glycol has an average molecular weight of about 300 to about 400.

5. A cosmetic comprising the gel of claim 1.

6. A dental care product comprising the gel of claim 1.

7. A method of gelling liquid polyethylene glycol, comprising combining a liquid polyethylene glycol having an average molecular weight of about 600 or less with water and a gelling effective amount of calcium acetate, wherein the resulting gel comprises about 40 to about 80 percent polyethylene glycol, about 1 to about 40 percent water, and about 0.5 to about 10 percent calcium acetate, by weight of the gel.

8. The method of claim 7 wherein said combining a liquid polyethylene glycol having an average molecular weight of about 600 or less with a gelling effective amount of calcium acetate is carried out a room temperature.

9. The method of claim 8 wherein said calcium acetate is in the form of an aqueous solution when it is combined with the polyethylene glycol.

10. The method of claim 7 wherein said gel has a turbidity less than about 1300 NTU.

11. The method of claim 7 wherein said gel comprises:
    about 50 to about 70 percent polyethylene glycol;
    about 5 to about 25 percent water; and
    about 0.5 to about 5 percent calcium acetate, by weight of the gel.

12. The method of claim 7 wherein said polyethylene glycol has an average molecular weight of about 300 to about 400.

13. The composition of claim 1 having a turbidity less than about 1300 NTU.

14. The composition of claim 1 wherein said gel is substantially translucent.

15. The method of claim 7 wherein the gelled polyethylene glycol is substantially translucent.

16. The method of claim 9 wherein said polyethylene glycol is combined with said aqueous solution of calcium acetate without any additional mixing.

* * * * *